United States Patent [19]

Elinov et al.

[11] 4,038,379

[45] July 26, 1977

[54] COMPOSITION FOR ROENTGENOSCOPY OF THE GASTROINTESTINAL TRACT CONTAINING A POLYSACCHARIDE STABILIZER

[76] Inventors: Nikolai Petrovich Elinov, ulitsa S. Kovalevskoi, 12, korpus 1, kv. 53; Isaak Yakovlevich Gurevich, prospekt Parkhomenko, 35/7, kv. 48; Afrikan Nikolaevich Dranishnikov, ulitsa Tambasova, 8, korpus 4, kv. 13; Nina Efimovna Goncharova, ulitsa Dobrovoltsev, 46, kv. 76, all of Leningrad, U.S.S.R.

[21] Appl. No.: 669,991

[22] Filed: Mar. 24, 1976

[51] Int. Cl.$^2$ .............................................. A61K 29/02
[52] U.S. Cl. ........................................ 424/4; 424/361; 536/1
[58] Field of Search ..................... 424/4, 361; 536/1

[56] References Cited

U.S. PATENT DOCUMENTS

| 3,447,940 | 6/1969 | Halleck | 536/1 X |
| 3,632,570 | 1/1972 | Gill | 536/1 |
| 3,784,681 | 1/1974 | Fischler | 424/4 |

*Primary Examiner*—Frederick E. Waddell
*Assistant Examiner*—Vera C. Clarke
*Attorney, Agent, or Firm*—Steinberg & Blake

[57] ABSTRACT

A substance for roentgenoscopy of the gastrointestinal tract, comprising barium sulphate in an amount of 5 to 40 per cent by weight, as stabilizer a polysaccharide of $\beta$-1,3-$\alpha$-1,4-$\alpha$-1,6-glucopyranosylglucose in an amount of 0.3 to 0.6 per cent by weight, and the rest being water.

Said substance remains stable for 90 days and, with periodic resuspending, for 1 year and longer.

3 Claims, No Drawings

COMPOSITION FOR ROENTGENOSCOPY OF THE GASTROINTESTINAL TRACT CONTAINING A POLYSACCHARIDE STABILIZER

The present invention relates to medicine, and, more specifically, to a substance for roentgenoscopy of the gastrointestinal tract.

It is known in the art that an aqueous suspension of barium sulphate is used for roentgenoscopy of the gastrointestinal tract. However, barium sulphate promptly precipitates when in the acidic environment of the stomach, and therefore fails to produce sharp X-ray pictures. To eliminate this disadvantage, various substances stabilizing the aqueous suspension of barium sulphate are employed. These substances include: pectin, anionogenic polysaccharide combined with high molecular weight substances, and the polysaccharide galactan. The use of methylcellulose for stabilizing aqueous solutions of barium sulphate is also known. The mentioned substances, however, stabilize aqueous suspensions of barium sulphate insufficiently.

Thus, e.g., an aqueous suspension of barium sulphate, containing methylcellulose, remains stable for only 2 or 3 days. Said suspension cannot be stored for long periods of time and resuspending fails to ensure required stability.

Although said stabilizing substances meet the requirements of roentgenoscopy, aqueous suspensions of barium sulphate containing said substances cannot be stored for long periods time, and therefore cannot be prepared several months in advance.

There are also known in the art aqueous suspensions of barium sulphate containing, apart from the above mentioned materials, surface-active substances as well. Although the surface-active substances do increase the stability of the suspension, they irritate the gastric and intestinal mucosa.

It is an object of the invention to provide a substance that stabilizes aqueous suspensions of barium sulphate for many days, without adding surface-active materials.

This object is attained by employing a polysaccharide of $\beta$-1, 3-$\alpha$-1,4- $\alpha$-1,6-glucopyranosylglucose as the stabilizer, the molecular weight thereof being about 9 million and its formula being as follows:

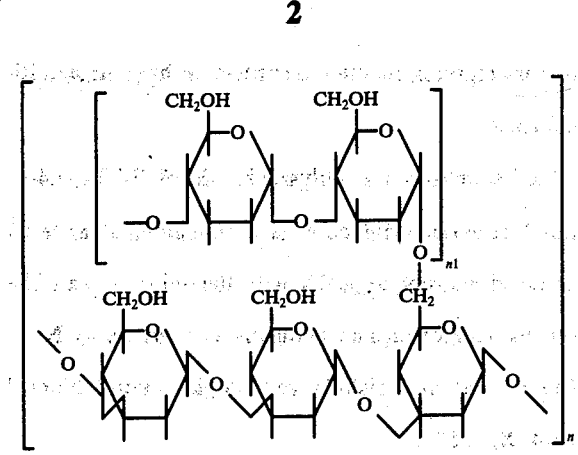

wherein: $n = 0.5-2$, and $\simeq 5 \cdot 10^3 - 9 \cdot 10^3$

In accordance with the invention, the substance intended for roentgenoscopy of the gastrointestinal tract contains 5 to 40 per cent by weight of barium sulphate, 0.3 to 0.6 per cent by weight of said polysaccharide, the rest being water.

Concentrations of said polysaccharide below 0.3 per cent by weight fail to ensure long-term stability of the suspension, while concentrations above 0.6 per cent are undesirable, since a gel is formed, and adequate stability is not ensured.

The substance in question may contain 5 to 7 percent by weight of glycerin which increases the stability of the suspension at low temperatures, specifically down to $-20°$ C.

To protect the polysaccharide from microbial effects in the course of long-term storage of the substance a preservative (merthiolate) is added, in an amount of about 0.001 percent by weight.

The invention permits increasing the stability of barium sulphate aqueous suspensions up to 90 days, and with periodical resuspending, up to 1 year and longer.

An aqueous suspension of barium sulphate containing the above stabilizer is readily restored following resuspending. In long-term storage, slight stratification is observed, but even slight shaking is sufficient for restoring the properties of the suspension.

The sedimentation stability of aqueous suspensions of barium sulphate and the resuspendibility thereof, when stabilized with said polysaccharide - $\beta$-I,3- $\alpha$-I,4- $\beta$-I,6-glucopyranosylglucose, are further illustrated in the following Table.

Table

| Barium sulphate, aqueous suspension | | Sedimentation, stability, days | | | | | Resuspendibility following storage (400 days) | Stability following resuspending (days) |
|---|---|---|---|---|---|---|---|---|
| barium sulphate % | stabilizer % | 1 | 10 | 30 | 60 | 80 | | |
| 5 | 0.3 | stable | | | | | readily | 7 to 10 |
| 10 | 0.3 | stable | | | | | readily | 7 to 10 |
| 20 | 0.3 | stable | | | | | readily | 7 to 10 |
| 30 | 0.6 | stable | | | | | readily | 7 to 10 |
| 40 | 0.6 | stable | | | | | readily | 7 to 10 |

An aqueous suspension of barium sulphate stabilized in accordance with the invention is recommended as an effective substance for reoentgenoscopy of the gastriontestinal tract.

Clinical trials of 20% and 40% aqueous suspensions of barium sulphate stabilized with the above properties and palatability thereof, a lack of any irritating effect upon the gastric and intestinal mucosa, and a lack of motor-emptying function disorders in the gastrointestinal tract.

Said stabilizer, viz. polysaccharide of β-I,3-α-1,4-α-I,6-glucopyranosylglucose, is a conventional material obtained microbiologically with the aid of a yeast-like fungus, Aureobadisium pullulans. (Cf. article by N. P. Elinov et al. in "Prikladnaya biologia i microbiologia" 1974, X, 4, 557).

The invention will be further understood from the following description of an exemplary preparation of said substance:

Example. 20 g of barium sulphate powder are mixed with 80 g of a 0.3% aqueous solution of polysaccharide of β-1,3-α-1,4-α-1,6-glucopyranosylglucose (pH 6.8-7.4) and dispersed in a mixer for 2 min. at 7,000 rpm. The thus received suspension is homogeneous and stable during storage for up to 3 months.

Said suspension is readily resuspended throughout the storage period (400 days), and remains homogeneous following resuspension for a few days thereafter.

What is claimed is:

1. A composition for roentgenoscopy of the gastrointestinal tract, comprising 5 to 40 percent by weight of barium sulphate, 0.3 to 0.6 percent by weight of polysaccharide of β-1,3-α-1,4-α-1,6-glucopyranosylglucose, the rest being water.

2. The composition according to claim 1, also containing 5 to 7 percent by weight of glycerin.

3. The composition according to claim 1, also containing about 0.001 percent by weight of merthiolate.

* * * * *